United States Patent [19]
Imura

[11] Patent Number: 6,020,959
[45] Date of Patent: Feb. 1, 2000

[54] APPARATUS AND METHOD FOR MEASURING SPECTRAL CHARACTERISTICS OF FLUORESCENT SAMPLE

[75] Inventor: Kenji Imura, Toyohashi, Japan

[73] Assignee: Minolta Co., Ltd., Osaka, Japan

[21] Appl. No.: 09/172,127

[22] Filed: Oct. 14, 1998

[30] Foreign Application Priority Data

Oct. 15, 1997 [JP] Japan ................................. 9-282257

[51] Int. Cl.⁷ ...................................................... G01J 3/42
[52] U.S. Cl. ...................................... 356/319; 250/461.1
[58] Field of Search .................................. 356/317, 318, 356/417, 72, 319, 326, 328, 445–448, 236; 250/458.1, 458.2, 461.1, 461.2, 228

[56] References Cited

U.S. PATENT DOCUMENTS 5,384,641  1/1995  Imura .
5,636,015  6/1997  Imura et al. .............................. 356/72

OTHER PUBLICATIONS

Japanese Industrial Standard, JIS 78717; Methods of Measurements for Colour of Fluorescent Objects, 1989.

Primary Examiner—K. P. Hantis
Attorney, Agent, or Firm—McDermott, Will & Emery

[57] ABSTRACT

An apparatus for measuring a spectral characteristic of a fluorescent sample, being provided with: a first illuminator for emitting a beam in a wavelength range including the ultraviolet spectrum; a second illuminator for emitting a beam in a wavelength range longer than a first cutoff wavelength; a spectral radiance factor measuring device for measuring first and second total spectral radiance factors of a fluorescent sample by illuminating the fluorescent sample by the first illumination device and second illumination device, respectively; a memory for storing weight coefficients for weighting first and second total spectral radiance factors; and a calculator for calculating a total spectral radiance factor of the fluorescent sample in accordance with the following equation using measured first and second total spectral radiance factors and a weight coefficient:

$$B_t(\lambda) = A(\lambda) \cdot Bt_1(\lambda) + \{1 - A(\lambda)\} \cdot Bt_2(\lambda)$$

wherein:

$Bt(\lambda)$: Total spectral radiance factor of the fluorescent sample
$A(\lambda)$: Weight coefficient
$Bt_1(\lambda)$: First total spectral radiance factor
$Bt_2(\lambda)$: Second total spectral radiance factor.

17 Claims, 7 Drawing Sheets

APPARATUS AND METHOD FOR MEASURING SPECTRAL CHARACTERISTICS OF FLUORESCENT SAMPLE

This application is based on patent application No. 9-282257 filed in Japan, from which priority is claimed.

BACKGROUND OF THE INVENTION

This invention relates to an apparatus and method for measuring spectral characteristics of a measurement sample containing a fluorescent substance.

In general, a visual characteristic of a sample containing a fluorescent substance (hereinafter, "fluorescent sample") can be expressed by a ratio of light emitted from the illuminated sample and light from a completely diffusive reflecting surface illuminated under the same conditions, i.e., a total spectral radiance factor. The total spectral radiance factor $Bt(\lambda)$ is given by the following Equation (1):

$$Bt(\lambda)=Br(\lambda)+Bf(\lambda) \qquad (1)$$

wherein $Br(\lambda)$, $Bf(\lambda)$ denote a reflected spectral radiance factor by reflected light components from the fluorescent sample and a fluorescent spectral radiance factor by fluorescent components from the fluorescent sample.

Particularly, a fluorescent sample containing an important fluorescent brightener is usually excited according to an excitation efficiency $P(\mu, \lambda)$ by an exited light of wavelength $\mu$ in an ultraviolet spectrum. Accordingly, the fluorescent spectral radiance factor $Bf(\lambda)$ at wavelength $\mu$ depends on a spectral intensity $I(\mu)$ of an illumination light as defined by the following Equation (2):

$$Bf(\lambda)=\int_{UV} I(\mu)P(\mu,\lambda)d\mu/Sn(\lambda) \qquad (2)$$

wherein $Sn(\lambda)$ denotes a relative spectral intensity of a standardized illumination light.

If $S_W(\lambda)$, $R_W(\lambda)$ denote spectral intensities of an emitted light and a reference light when a nonfluorescent white standard sample having a known spectral reflectance $W(\lambda)$, and $S(\lambda)$, $R(\lambda)$ denote spectral intensities of an emitted light and a reference light when the sample is measured by a colorimeter, the total spectral radiance factor $Bt(\lambda)$ is given by the following Equation (3):

$$Bt(\lambda)=W(\lambda)\cdot(S(\lambda)/R(\lambda))/(S_W(\lambda)/R_W(\lambda)) \qquad (3)$$

However, for the aforementioned reason, the spectral intensity of the illumination light needs to correspond with the spectral intensity of the light used for a supposed colorimetry in the case that a fluorescent sample is measured.

The lights used for the colorimetry include D50, D55, D75 (daylight), F1, F3, F11 (fluorescent lamp) as well as standard lights such as D65 (daylight) and A (incandescent light source) whose spectral intensities are defined by the CIE (Committee on the International Illumination). For fluorescent samples, standard light D65 is usually used.

However, since it is very difficult to obtain an illumination light source approximate to the standard light D65, a relative intensity in the ultraviolet spectrum has conventionally been adjusted according to a method as shown in FIG. 7 ("Assessment of Whiteness and Tint of Fluorescent Substrates with Good Instrument Correlation" by Rolf Griesser, "The Calibration of Instruments for the Measurement of Paper Whiteness" by Anthony Bristow in "COLOR Research and Application, Vol. 19, No. 6, Dec. 1994).

In FIG. 7, a fluorescent sample 1 is placed on a sample aperture 21 of an integrating sphere 2. A light source 101 such as a xenon lamp having a sufficient intensity in the ultraviolet spectrum is driven by a light emission circuit 104 and a beam 102 is introduced into the integrating sphere 2 through an aperture 23. Here, an ultraviolet cutoff filter 103 is inserted so as to partially cut off the beam 102. Accordingly, the beam having transmitted through the ultraviolet cutoff filter 103 has ultraviolet components removed therefrom. The degree of insertion of the ultraviolet cutoff filter 103 is adjustable so as to adjust a relative ultraviolet intensity of the illumination light.

The beam 102 introduced into the integrating sphere 2 undergoes a multiple diffusion/reflection therein to become a diffused light and illuminates the fluorescent sample 1. Light comprised of components in a specified direction emitted from the illuminated sample 1 is incident on a spectral device 105 for the sample through an observation aperture 24, whereby a spectral intensity $S(\mu)$ is detected. Simultaneously, a beam 62 having substantially same spectral intensity as the illumination light of the fluorescent sample 1 is incident on a reference fiber 61 to be introduced to a spectral device 106 for the reference, whereby a spectral intensity $R(\lambda)$ is detected.

In order to adjust a relative intensity in the ultraviolet spectrum, a nonfluorescent white standard sample 12 having a known spectral reflectance $W(\lambda)$ is first measured, and then a standard fluorescent sample 13 having one known color value of those obtained when being illuminated by a standard light for the colorimetry, e.g., ICE whiteness is measured. The degree of insertion of the ultraviolet filter 103 is so adjusted that the CIE whiteness calculated from the total spectral radiance factor $Bt(\lambda)$ obtained from Equation (3) agrees with the known CIE whiteness. At this time, Equation (2) can be rewritten into the following Equation (4):

$$Bf(\lambda)=\int_{UV} \alpha\cdot I(\mu)P(\mu,\lambda)d\mu/Sn(\lambda) \qquad (4)$$

wherein $\alpha$ denotes an attenuation coefficient in the ultraviolet spectrum.

A known apparatus is provided with a first light source for irradiating a beam containing light components in the ultraviolet spectrum and a second light source for irradiating a beam containing light components outside the ultraviolet spectrum (see U.S. Pat. No. 5,636,015). In this apparatus, the spectral intensity of the light emitted from a sample upon being illuminated by the illumination lights from the first and second light sources are weighted and the spectral intensities of the illumination lights from the first and second light sources are weighted as seen in Equation (8) of this publication.

In the prior art shown in FIG. 7, the relative ultraviolet intensity of the illumination light can be so adjusted as to give the same CIE whiteness as when illuminated by the standard illumination light for the colorimetry for the same fluorescent sample as or the one similar to the standard fluorescent sample used for the adjustment of the relative intensity in the ultraviolet spectrum.

However, a highly accurate measurement may not be conducted since other color values such as tints at that time may not necessarily be same. Further, since the measurement and the movement of the filter need to be repeated for the intensity adjustment in the ultraviolet spectrum, it takes a time to obtain a measurement result.

As described above, in the apparatus disclosed in U.S. Pat. No. 5,636,015, the spectral intensity of the light emitted from the sample and that of the illumination light illuminating the sample are weighted, respectively. Accordingly, if the spectral intensity of the illumination light varies, the weighted result varies even if the same sample is used. In other words, relative variations of the spectral intensities of the illumination lights from the first and second light sources adversely affect the total spectral radiance factor.

SUMMARY OF THE INVENTION

It is an object of the present invention to provide an apparatus and method for measuring spectral characteristics of a fluorescent sample which have overcome the problems residing in the prior art. According to an aspect of the invention, an apparatus for measuring a spectral characteristic of a fluorescent sample, comprising: a first illumination device which emits a beam in a wavelength range including the ultraviolet spectrum; a second illumination device which emits a beam in a wavelength range longer than a first cutoff wavelength; a spectral radiance factor measuring device which measures a first total spectral radiance factor of a fluorescent sample placed in a measurement position by illuminating the fluorescent sample by the first illumination device, and a second total spectral radiance factor of the fluorescent sample by illuminating the fluorescent sample by the second illumination device; a storage device which stores weight coefficients for weighting first and second total spectral radiance factors, each weight coefficient being calculated for each wavelength; and a calculator which calculates a total spectral radiance factor of the fluorescent sample in accordance with the following equation using measured first and second total spectral radiance factors and a weight coefficient:

$$B_t(\lambda) = A(\lambda) \cdot Bt_1(\lambda) + \{1 - A(\lambda)\} \cdot Bt_2(\lambda)$$

wherein:

Bt($\lambda$): Total spectral radiance factor of the fluorescent sample

A($\lambda$): Weight coefficient $Bt_1(\lambda)$: First total spectral radiance factor $Bt_2(\lambda)$: Second total spectral radiance factor.

According to another aspect of the invention, an apparatus for measuring a spectral characteristic of a fluorescent sample, comprising: a first illumination device which emits a beam in a wavelength range including the ultraviolet spectrum; a second illumination device which emits a beam in a wavelength range longer than a first cutoff wavelength; a third illumination device which emits a beam in a wavelength range longer than a second cutoff wavelength different from the first cutoff wavelength; a spectral radiance factor measuring device which measures a first total spectral radiance factor of a fluorescent sample placed in a measurement position by illuminating the fluorescent sample by the first illumination device, and a second total spectral radiance factor of the fluorescent sample by illuminating the fluorescent sample by the second illumination device, and a third total spectral radiance factor of the fluorescent sample by illuminating the fluorescent sample by the third illumination device; a storage device which stores first and second weight coefficients for weighting first, second, and third total spectral radiance factors, the first and second weight coefficients being calculated for each wavelength; and a calculator which calculates a total spectral radiance factor of the fluorescent sample in accordance with the following equation using measured first, second, and third total spectral radiance factors and the first and second weight coefficients:

$$Bt(\lambda) = A_1(\lambda) \cdot Bt_1(\lambda) + A_2(\lambda) \cdot Bt_2(\lambda) + \{1 - A_1(\lambda) - A_2(\lambda)\} \cdot Bt_3(\lambda)$$

wherein:

Bt($\lambda$): Total spectral radiance factor of the fluorescent sample $A_1(\lambda)$: First weight coefficient $A_2(\lambda)$: Second weight coefficient $Bt_1(\lambda)$: First total spectral radiance factor $Bt_2(\lambda)$: Second total spectral radiance factor $Bt_3(\lambda)$: Third total spectral radiance factor.

According to still another aspect of the invention, an apparatus for measuring a spectral characteristic of a fluorescent sample, comprising: a first illumination device which emits a beam in a wavelength range including the ultraviolet spectrum; a second illumination device which emits a beam in a wavelength excluding the ultraviolet spectrum; a first measuring device which measures a first spectral characteristic value of a fluorescent sample placed in a measurement position by illuminating the fluorescent sample by the first illumination device; a second measuring device which measures a second spectral characteristic value of the fluorescent sample by illuminating the fluorescent sample by the second illumination device; a total spectral characteristic value calculator which calculates a total spectral characteristic value of the fluorescent sample using measured first and second spectral characteristic values and a weight coefficient: and a weight coefficient calculator which calculates a weight coefficient to minimize a sum of respective squares of differences between total spectral characteristic values of a plurality of standard fluorescent samples and known total spectral characteristic values of the plurality of standard fluorescent samples.

According to yet still another aspect of the invention, a method for measuring a spectral characteristic of a fluorescent sample, comprising the steps of: measuring a first total spectral radiance factor of a fluorescent sample placed in a measurement position by illuminating the fluorescent sample by a first illumination device emitting a beam in a wavelength range including the ultraviolet spectrum; measuring a second total spectral radiance factor of the fluorescent sample by illuminating the fluorescent sample by a second illumination device emitting a beam in a wavelength range longer than a first cutoff wavelength; calculating a total spectral radiance factor of the fluorescent sample in accordance with the following equation using measured first and second total spectral radiance factors and a weight coefficient:

$$B_t(\lambda) = A(\lambda) \cdot Bt_1(\lambda) + \{1 - A(\lambda)\} \cdot Bt_2(\lambda)$$

wherein:

Bt($\lambda$): Total spectral radiance factor of the fluorescent sample

A($\lambda$): Weight coefficient $Bt_1(\lambda)$: First total spectral radiance factor $Bt_2(\lambda)$: Second total spectral radiance factor.

According to further another aspect of the invention, a method for measuring a spectral characteristic of a fluorescent sample, comprising the steps of: measuring a first total spectral radiance factor of a fluorescent sample placed in a measurement position by illuminating the fluorescent sample by a first illumination device emitting a beam in a wavelength range including the ultraviolet spectrum; measuring a second total spectral radiance factor of the fluorescent sample by illuminating the fluorescent sample by a second illumination device emitting a beam in a wavelength range longer than a first cutoff wavelength; measuring a third total spectral radiance factor of the fluorescent sample by illuminating the fluorescent sample by a third illumination device emitting a beam in a wavelength range longer than a second cutoff wavelength different from the first cutoff wavelength; and calculating a total spectral radiance factor of the fluorescent sample in accordance with the following equation using measured first, second, and third total spectral radiance factors and first and second weight coefficients:

$$Bt(\lambda)=A_1(\lambda)\cdot Bt_1(\lambda)+A_2(\lambda)\cdot Bt_2(\lambda)+\{1-A_1(\lambda)-A_2(\lambda)\}\cdot Bt_3(\lambda)$$

wherein:

$Bt(\lambda)$: Total spectral radiance factor of the fluorescent sample $A_1(\lambda)$: First weight coefficient $A_2(\lambda)$: Second weight coefficient $Bt_1(\lambda)$: First total spectral radiance factor $Bt_2(\lambda)$: Second total spectral radiance factor $Bt_3(\lambda)$: Third total spectral radiance factor.

These and other objects, features and advantages of the present invention will become more apparent upon a reading of the following detailed description and accompanying drawings.

DETAILED DESCRIPTION OF THE PREFERRED EMBODIMENTS OF THE INVENTION

Figure 1:
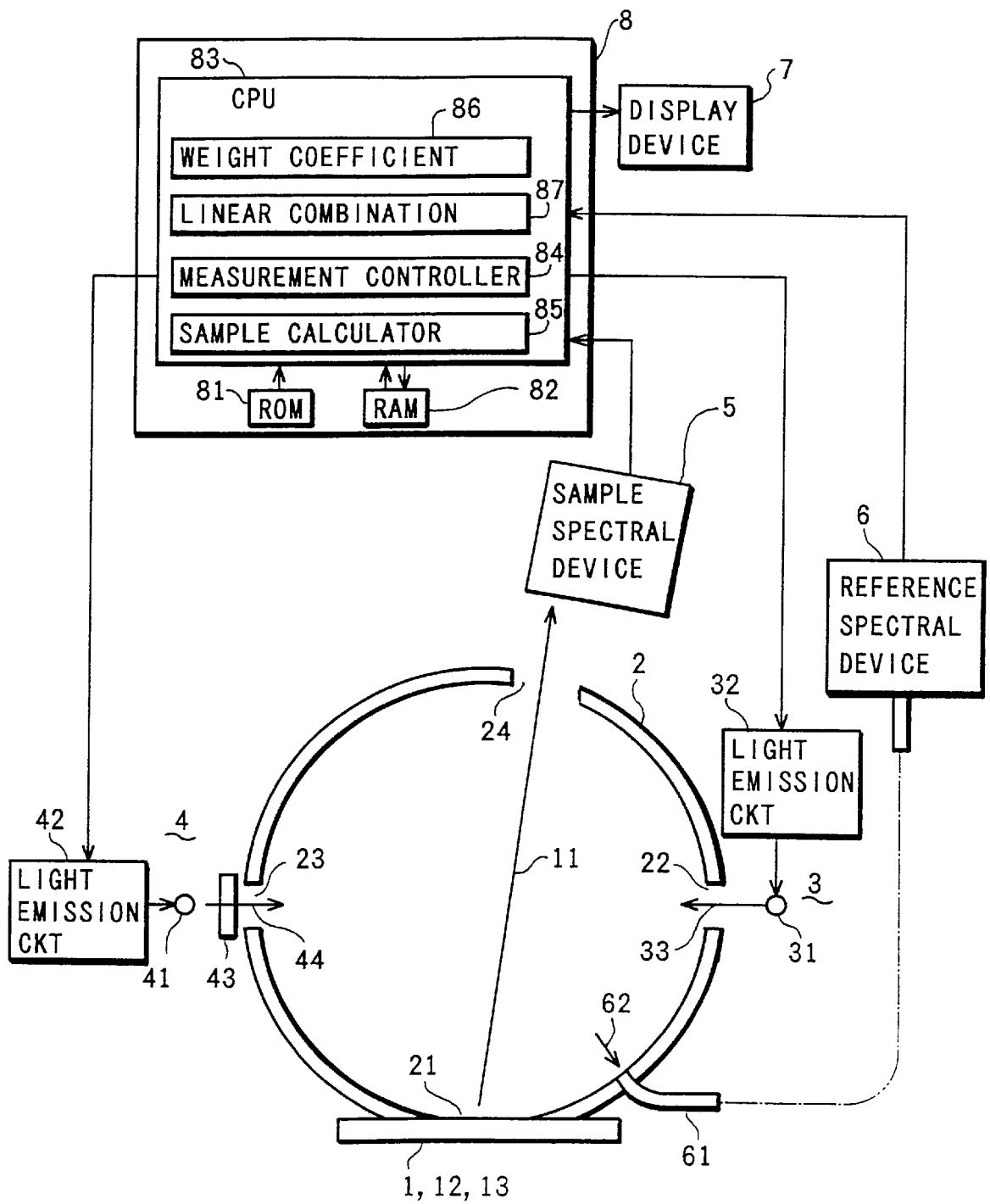
FIG. 1 is a diagram showing a construction of an apparatus for measuring spectral characteristics of a fluorescent sample, according to a first embodiment of the invention.

Referring to FIG. 1 showing a construction of an apparatus for measuring spectral characteristics of a fluorescent sample, according to a first embodiment of the invention, an integrating sphere 2 has a white diffusion/reflection paint such as MgO or $BaSO_4$ applied to its inner wall for the multiple diffusion/reflection of an incident beam to produce a diffused illumination light, and is provided with a sample aperture 21, light source apertures 22, 23 and an observation aperture 24 which are formed in specified positions. A fluorescent sample 1 is a sample to be measured and is comprised of fibers, paper product or the like containing a fluorescent substance. The fluorescent sample 1 is placed at the sample aperture 21 (measurement position) of the integrating sphere 2.

At the sample aperture 21 of the integrating sphere 2 are also placed a nonfluorescent white standard sample 12 having a known spectral reflectance $W(\lambda)$ used to correct the reflectance and a standard fluorescent sample 13 having a known total spectral radiance factor $Bt_D(\lambda)$ when illumination is made by light for a supposed colorimetry.

A first illumination unit 3 includes a light source 31 and a light emission circuit 32. The light source 31 is, e.g., a xenon flash lamp or the like for irradiating a beam containing light components in the ultraviolet spectrum and is arranged in vicinity of the light source aperture 22 of the integrating sphere 2. The light emission circuit 32 turns the light source 31 on and off to emit a pulse of light. A pulsed beam 33 containing light components in the ultraviolet spectrum is introduced into the integrating sphere 2 through the light source aperture 22.

The second illumination unit 4 includes a light source 41, a light emission circuit 42 and a cutoff filter 43. The light source 41 is, e.g., a xenon flash lamp and is arranged at the light source aperture 23 of the integrating sphere 2. The cutoff filter 43 is arranged between the light source 41 and the light source aperture 23 to transmit only beams in a wavelength range longer than a first cutoff wavelength $\lambda_{C1}$ (e.g., $\lambda_{C1}=400$ nm in this embodiment), thereby removing the light components in the ultraviolet spectrum below a wavelength of 400 nm from the incident light from the light source 41. The light emission circuit 42 turns the light source 41 on and off to emit a pulse of light. A pulsed beam having its light components in the ultraviolet spectrum removed by the cutoff filter 43 is introduced into the integrating sphere 2 through the light source aperture 23.

The beams 33, 44 introduced into the integrating sphere 2 are caused to undergo multiple diffusion/reflection by the inner wall of the integrating sphere 2, thereby diffusely illuminating the fluorescent sample 1. Among lights emitted from the surface of the illuminated fluorescent sample 1, light 11 containing components of a specified direction emerges from the integrating sphere 2 through the observation aperture 24 and is incident on a sample spectral device 5 arranged at the observation aperture 24. The sample spectral device 5 detects the spectral intensity of the light 11 and the detected spectral intensity is sent to a controller 8 to be described later.

An incident end of an optical fiber 61 for the reference is arranged in vicinity of the sample aperture 21 of the integrating sphere 2. An emergent end of the optical fiber 61 is connected with a reference spectral device 6 to introduce a reference light 62 having substantially the same spectral intensity as the illumination light for the sample incident on the incident end to the reference spectral device 6. The reference spectral device 6 monitors the illumination light by detecting the spectral intensity of the reference light 62, and the detected spectral intensity data is sent to the controller 8. A display device 7 is comprised of, e.g., a CRT for display calculation results such as a total spectral radiance factor calculated by the controller 8.

The controller 8 controls the entire operation of the measuring apparatus including a display content of the display device 7. The controller 8 includes a ROM 81, a RAM 82 and a CPU 83 which is provided with a measurement controller 84, a sample calculator 85, a weight coefficient calculator 86 and a linear combination calculator 87 as function blocks as shown in FIG. 1. The CPU 83 is connected with the sample spectral device 5, the reference spectral device 6, the display device 7 and the light emission circuits 32, 42.

The ROM 81 stores a control program of the CPU 83 and preset data including the known spectral reflectance $W(\lambda)$ of the nonfluorescent white standard sample 12 and the known total spectral radiance factor $Bt_D(\lambda)$ of the standard fluorescent sample 13. The RAM 82 temporarily stores data such as measurement results.

The measurement controller 84 controllably turns the light sources 31, 41 by controllably driving the light emission circuits 32, 42 when the sample 1, 12 or 13 is placed at the sample aperture 21 and causes data including the spectral intensities obtained by the sample spectral device 5 and the reference spectral device 6 to be stored in the RAM 82.

The sample calculator 85 calculates a first total spectral radiance factor $Bt_1(\lambda)$ when the fluorescent sample 1 is illuminated by the first illumination unit 3 and a second total spectral radiance factor $Bt_2(\lambda)$ when it is illuminated by the second illumination unit 4 based on the data including the spectral intensities obtained by the sample spectral device 5 and the reference spectral device 6 in a procedure to be described later, and causes the calculation results to be stored in the RAM 82.

The weight coefficient calculator 86 calculates the weight coefficient $A(\lambda)$ of the first and second total spectral radiance factors $Bt_1(\lambda)$, $Bt_2(\lambda)$ in a procedure to be described later and causes the calculation results to be stored in the RAM 82.

The linear combination calculator 87 calculates the total spectral radiance factor $Bt(\lambda)$ of the fluorescent sample 1 by linearly combining the first and second total spectral radiance factors $Bt_1(\lambda)$, $Bt_2(\lambda)$ using the weight coefficient $A(\lambda)$ stored in the RAM 82 in a procedure to be described later.

The spectral radiance factor measuring device is constructed by the sample spectral device 5, the reference spectral device 6 and the sample calculator 85 of the CPU 83.

The CPU 83 may be provided with a calculator for calculating an other index value such as a color value from the calculated total spectral radiance factor $Bt(\lambda)$.

Figure 2:
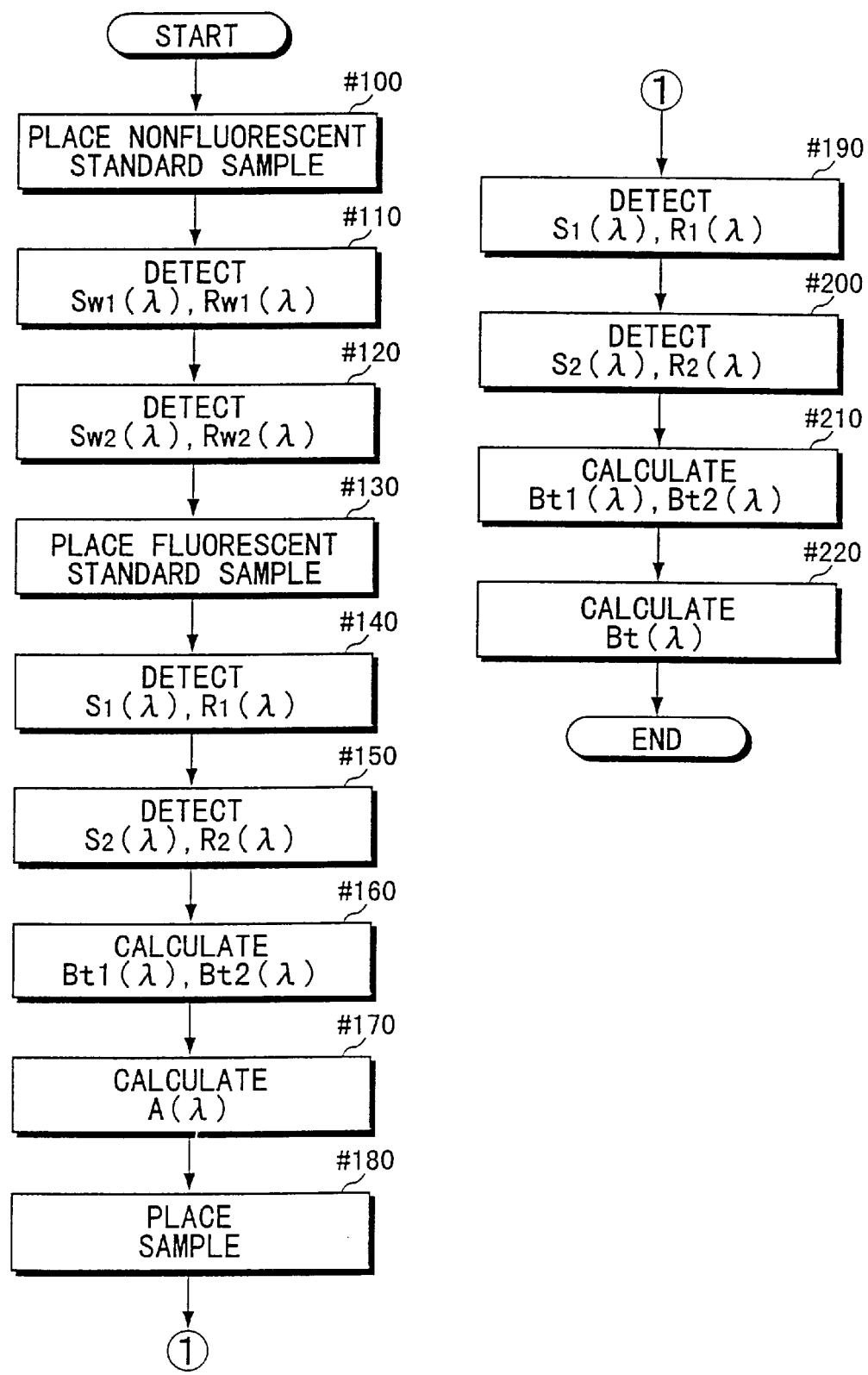
FIG. 2 is a flowchart showing a procedure of calculating a total spectral radiance factor $Bt(\lambda)$ by measuring the fluorescent sample.

Next, with reference to FIG. 1, the procedure for calculating the total spectral radiance factor $Bt(\lambda)$ by measuring the fluorescent sample 1 in accordance with a flowchart of FIG. 2 is described.

First, reflectance is corrected using the nonfluorescent white standard sample 12 not containing a fluorescent substance. Specifically, the nonfluorescent white standard sample 12 having a known spectral reflectance $W(\lambda)$ is placed at the sample aperture 21 (Step #100). In this state, the light source 31 is caused to emit a pulse of light by the measurement controller 84, and a spectral intensity $S_{W1}(\lambda)$ of the emitted light 11 from the nonfluorescent white standard sample 12 is detected and a spectral intensity $R_{W1}(\lambda)$ of the reference time at that time is detected. The detected spectral intensities $S_{W1}(\lambda)$, $R_{W1}(\lambda)$ are stored in the RAM 82 (Step #110).

Subsequently, the light source 41 is turned to emit a pulse of light by the measurement controller 84. Similar to the above, spectral intensities $S_{W2}(\lambda)$, $R_{W2}(\lambda)$ of the emitted light 11 from the nonfluorescent white standard sample 12 and of the reference light 62 at that time are detected and stored in the RAM 82 (Step #120).

Subsequently, relative intensities in the ultraviolet spectrum are corrected using the standard fluorescent sample 13 having a known total spectral radiance factor $Bt_D(\lambda)$ when being illuminated by light for a supposed colorimetry (e.g., standard light D65 in this embodiment).

Specifically, the standard fluorescent sample 13 is placed at the sample aperture 21 (Step #130). In this state, the light source 31 is turned on to emit a pulse of light by the measurement controller 84, and spectral intensities $S_1(\lambda)$, $R_1(\lambda)$ of the emitted light 11 from the standard fluorescent sample 13 and of the reference light 62 at that time are detected and stored in the RAM 82 (Step #140).

Subsequently, the light source 41 is turned on to emit a pulse of light by the measurement controller 84. Similar to the above, spectral intensities $S_2(\lambda)$, $R_2(\lambda)$ of the emitted light 11 from the standard fluorescent sample 13 and of the reference light 62 at that time are detected and stored in the RAM 82 (Step #150).

The first and second total spectral radiance factors $Bt_1(\lambda)$, $Bt_2(\lambda)$ are calculated in accordance with the following Equation (5) by the sample calculator 85 using the respective spectral intensity data $S_{W1}(\lambda)$, $R_{W1}(\lambda)$, $S_{W2}(\lambda)$, $R_{W2}(\lambda)$, $S_1(\lambda)$, $R_1(\lambda)$, $S_2(\lambda)$, $R_2(\lambda)$ stored in the RAM 82 (Step #160).

$$Bt_1(\lambda)=W(\lambda)\cdot\{S_1(\lambda)/R_1(\lambda)\}/\{S_{W1}(\lambda)/R_{W1}(\lambda)\}$$
$$Bt_2(\lambda)=W(\lambda)\cdot\{S_2(\lambda)/R_2(\lambda)\}/\{S_{W2}(\lambda)/R_{W2}(\lambda)\} \quad (5)$$

Subsequently, the weight coefficient $A(\lambda)$ is calculated for each wavelength such that a combined total spectral radiance factor $Bt(\lambda)$ given by the following Equation (6) which is obtained by weighting the first and second total spectral radiance factors $Bt_1(\lambda)$, $Bt_2(\lambda)$ by the weight coefficient $A(\lambda)$ by the weight coefficient calculator 86 and linearly combining the weighted ratios $Bt_1(\lambda)$, $Bt_2(\lambda)$ becomes equal to the known total spectral radiance factor $Bt_D(\lambda)$ of the standard fluorescent sample 13 stored in the ROM 81, and stored in the RAM 82 (Step #170).

$$Bt(\lambda)=A(\lambda)\cdot Bt_1(\lambda)+\{1-A(\lambda)\}\cdot Bt_2(\lambda) \quad (6)$$

Subsequently, the fluorescent sample 1 to be measured is placed at the sample aperture 21 (Step #180). In this state, the light source 31 is turned on to emit a pulse of light by the measurement controller 84, the spectral intensities $S_1(\lambda)$, $R_1(\lambda)$ of the emitted light 11 from the fluorescent sample 1 and the reference light 62 at that time are detected and stored in the RAM 82 (Step #190).

Subsequently, the light source 41 is turned on to emit a pulse of light by the measurement controller 84. Similar to the above, the spectral intensities $S_2(\lambda)$, $R_2(\lambda)$ of the emitted light 11 from the fluorescent sample 1 and of the reference light 62 at that time are detected and stored in the RAM 82 (Step #200).

The first and second total spectral radiance factors $Bt_1(\lambda)$, $Bt_2(\lambda)$ are then calculated in accordance with Equation (5) (Step #210).

Subsequently, the combined total spectral radiance factor $Bt(\lambda)$ given by Equation (6) which is obtained by weighting the first and second total spectral radiance factors $Bt_1(\lambda)$, $Bt_2(\lambda)$ by the weight coefficient $A(\lambda)$ stored in the RAM 82 and linearly combining them is calculated as a total spectral radiance factor of the fluorescent sample 1 by the linear combination calculator 87 (Step #220).

As described above, according to the first embodiment, the relative intensities in the ultraviolet spectrum can accurately be corrected by using the standard fluorescent sample 13 having the known total spectral radiance factor $Bt_D(\lambda)$ As seen from Equation (5), since the first and second spectral radiance factors $Bt_1(\lambda)$, $Bt_2(\lambda)$ have a ratio of the emitted light from the standard fluorescent sample 13 to the reference light as a factor, an influence caused by a relative variation of the spectral intensities of the light sources 31, 41 can be eliminated and, therefore, the weight coefficient $A(\lambda)$ can accurately be calculated.

Further, the apparatus has no mechanical movable portion. Accordingly, by calculating the weight coefficient $A(\lambda)$ using the standard fluorescent sample 13 and store it in the RAM 82, a measurement can be made for the fluorescent sample 1 having characteristics similar to those of the standard fluorescent sample 13 within a very short period.

Furthermore, in the case that the characteristics of the florescent sample 1 to be measured are identical to or approximate to those of the standard fluorescent sample 13, the total spectral radiance factor $Bt(\lambda)$ substantially agrees with the total spectral radiance factor $Bt_D(\lambda)$ when illumination is made by the light for the supposed colorimetry. Accordingly, all color values calculated from the total spectral radiance factor $Bt(\lambda)$ can be caused to agree with the color values when illumination is made by the light for the supposed colorimetry (standard light D65 in this embodiment).

A reflection spectral radiance factor $Br(\lambda)$ is not dependent on the spectral intensity of the illumination light. On the other hand, a fluorescent spectral radiance factor $Bf(\lambda)$ depends on the spectral intensity of the illumination light, particularly in the ultraviolet spectrum and differs between the first and second illumination units 3 and 4.

Accordingly, the linear combination of the first and second total spectral radiance factors $Bt_1(\lambda)$, $Bt2(\lambda)$ using the weight coefficient $A(\lambda)$ having a wavelength dependence means that the relative intensity of the fluorescent spectral radiance factor $Bf(\lambda)$ to the reflection spectral radiance factor $Br(\lambda)$ at a wavelength $\lambda$ in the visible spectrum is adjusted for each wavelength by adjusting the intensity in the ultraviolet spectrum corresponding to the intensity of the illumination light at this wavelength.

Figure 7:
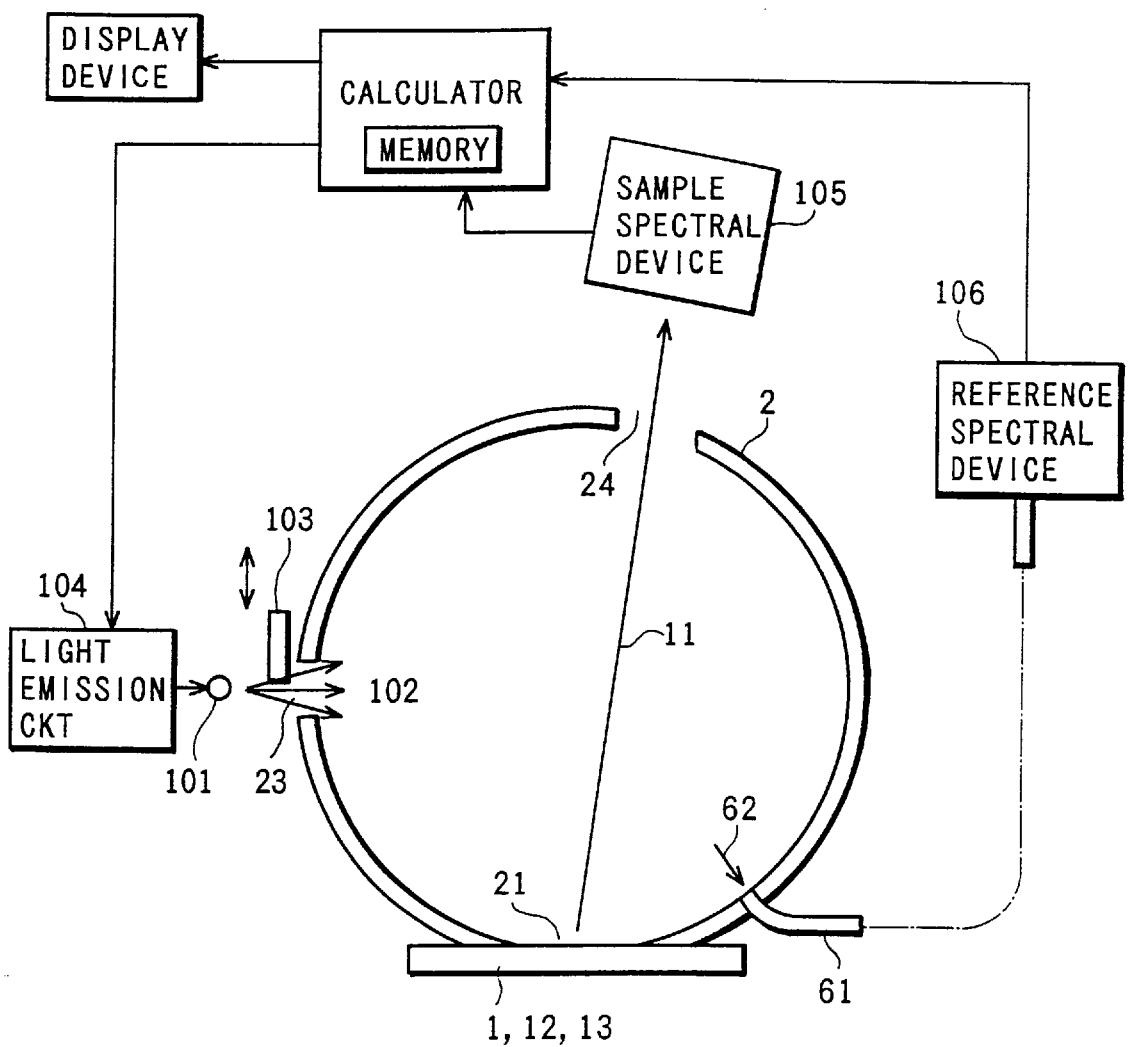
FIG. 7 is a diagram showing a construction of a conventional apparatus for measuring spectral characteristics of a fluorescent sample.

This is equivalent to performing the adjustment of the relative intensity in the ultraviolet spectrum by the degree of insertion of the ultraviolet cutoff filter described with reference to FIG. 7 for each wavelength of the visible spectrum. In this case, Equation (4) is written into the following Equation (7).

$$Bf(\lambda) = \int_{UV} Q(\lambda) \cdot I(\mu) P(\mu, \lambda) d\mu / Sn(\lambda) \quad (7)$$

wherein $Q(\lambda)$ is a degree of attenuation of the ultraviolet intensity dependent on an observed wavelength $\lambda$ of the visible spectrum.

Figure 3A:
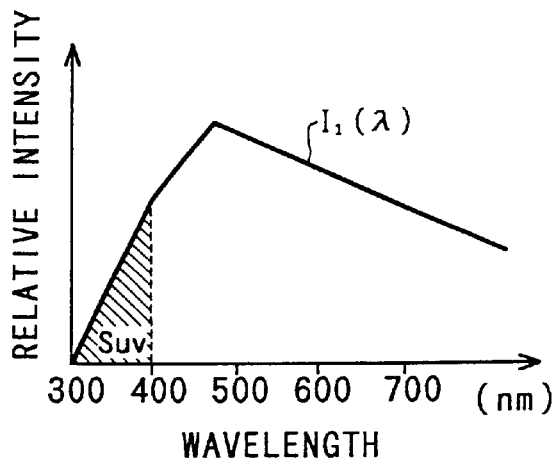
FIGS. 3A to 3E are graphs showing an illumination light equivalently produced by weighting total spectral radiance factors $Bt_1(\lambda)$, $Bt_2(\lambda)$ by a weight coefficient $A(\lambda)$ by first and second illumination units and linearly combining them.
Figure 3B:
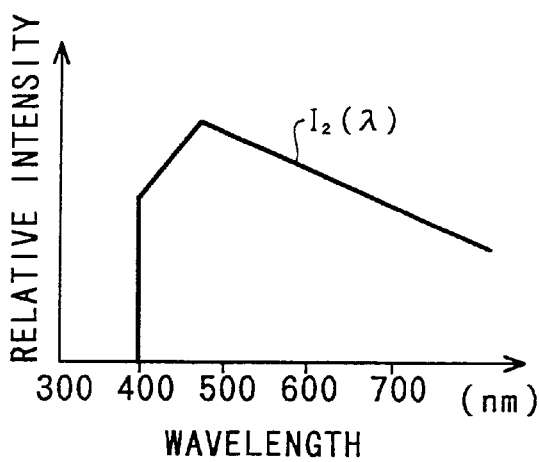
Figure 3C:
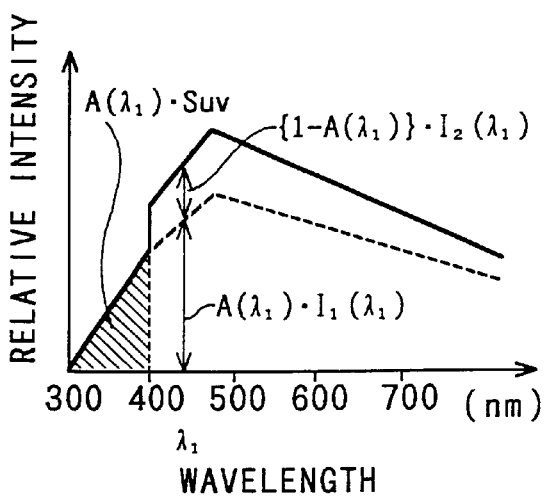
Figure 3D:
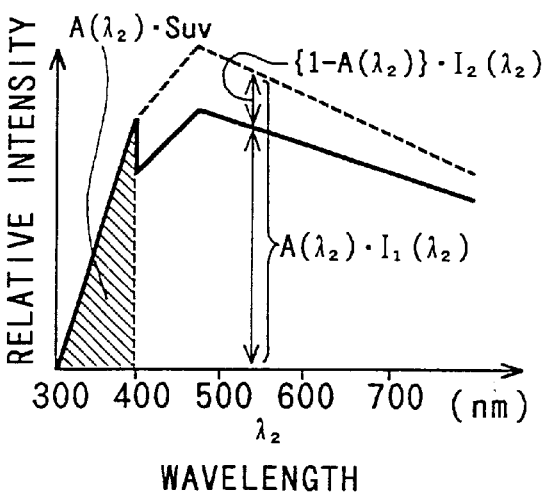
Figure 3E:
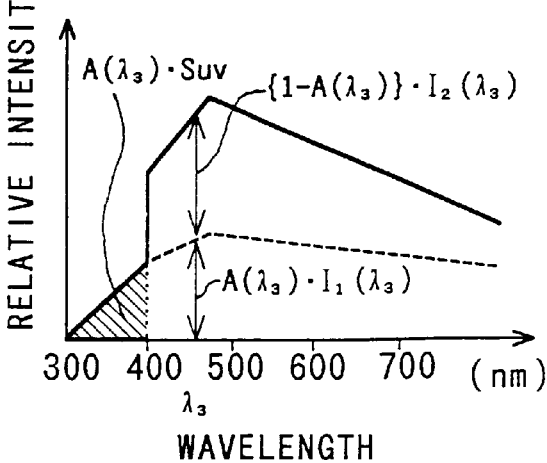

FIGS. 3A to 3E are graphs showing an illumination light equivalently combined by weighting the first and second total spectral radiance factors $Bt_1(\lambda)$, $Bt_2(\lambda)$ by the first and second illumination units 3, 4 by the weight coefficient $A(\lambda)$ and linearly combining them. Specifically, FIG. 3A shows the spectral intensity $I_1(\lambda)$ of the first illumination unit 3, FIG. 3B shows the spectral intensity $I_2(\lambda)$ of the second illumination unit 4, FIG. 3C shows a spectral intensity $A(\lambda_1) \cdot I_1(\lambda_1) + \{1 A(\lambda_1)\} \cdot I_2(\lambda_1)$ of the combined illumination light when $\lambda = \lambda_1$ wherein $A(\lambda_1) \leq 1$, FIG. 3D shows a spectral intensity $A(\lambda_2) \cdot I_1(\lambda_2) + \{1 - A(\lambda_2)\} \cdot I_2(\lambda_2)$ of the combined illumination light when $\lambda = \lambda_2$ wherein $A(\lambda_2) > 1$, and FIG. 3E shows a spectral intensity $A(\lambda_3) \cdot I_1(\lambda_3) + \{1 - A(\lambda_3)\} \cdot I_2(\lambda_3)$ of the combined illumination light when $\lambda = \lambda_3$ wherein $A(\lambda_3) \leq 1$. It should be appreciated that $S_{UV}$ denotes an area of the spectral intensity at and below the wavelength 400 nm and represents the spectral intensity of the entire ultraviolet spectrum.

Figure 4A:
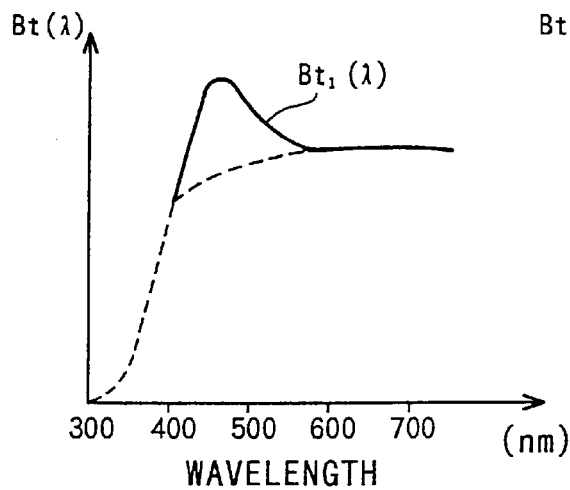
FIGS. 4A to 4D are graphs showing the total spectral radiance factor $Bt(\lambda)$ in the graphs of FIGS. 3A to 3D.
Figure 4B:
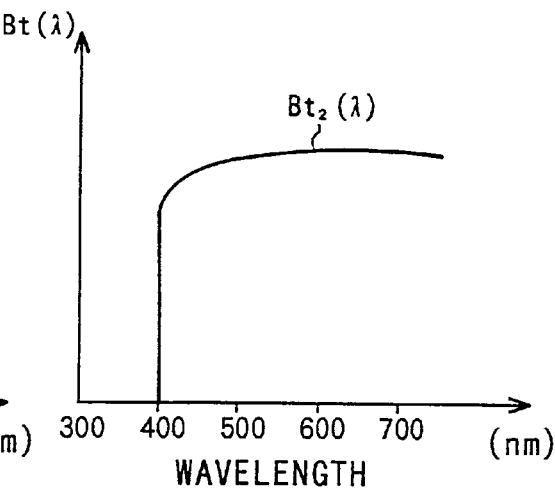
Figure 4C:
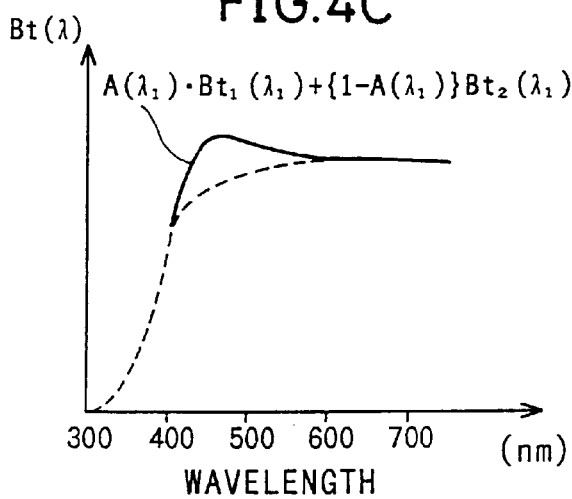
Figure 4D:
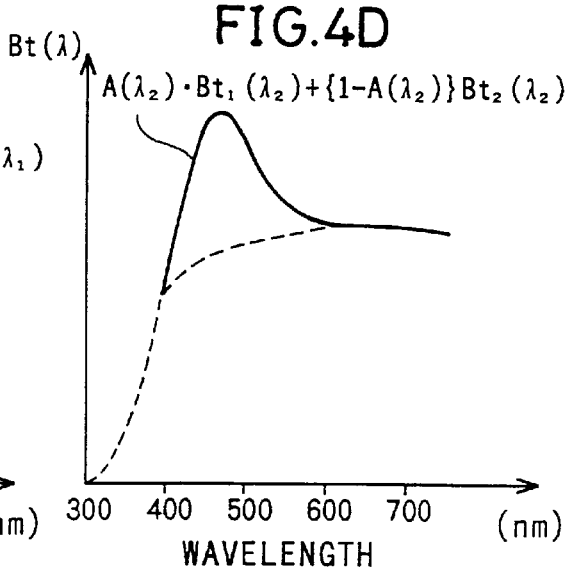

FIGS. 4A to 4D are graphs showing the total spectral radiance factor $Bt(\lambda)$ in FIGS. 3A to 3D, respectively. Specifically, FIG. 4A shows the total spectral radiance factor $Bt(\lambda)$ when the sample is illuminated by the first illumination unit 3, FIG. 4B shows the total spectral radiance factor $Bt(\lambda)$ when the sample is illuminated by the second illumination unit 4, FIG. 4C shows the combined total spectral radiance factor $Bt(\lambda)$ obtained by Equation (6) by applying the weight coefficient $A(\lambda)$ of FIG. 3C to the total spectral radiance factors $Bt_1(\lambda)$, $Bt_2(\lambda)$ of FIGS. 3A and 3B, and FIG. 4D shows the combined total spectral radiance factor $Bt(\lambda)$ obtained by Equation (6) by applying the weight coefficient $A(\lambda)$ of FIG. 3D to the total spectral radiance factors $Bt_1(\lambda)$, $Bt_2(\lambda)$ of FIGS. 3A and 3B.

It should be noted that, in actuality, not the combined illumination light, but the combined total spectral radiance factor is calculated.

In FIGS. 3A to 3E, if a ratio $S_{UV}/I(\lambda)$ of the spectral intensity $S_{UV}$ of the entire ultraviolet spectrum to the spectral intensity $I(\lambda)$ at wavelength $\lambda$ of the visible region of the combined illumination light is compared with a ratio $S_{UV}/I_1(\lambda)$ of the spectral intensity $S_{UV}$ to the spectral intensity $I_1(\lambda)$ of the first illumination unit 3 shown in FIG. 3A, $S_{UV}/I(\lambda) < S_{UV}/I_1(\lambda)$ in FIG. 3C, whereas $S_{UV}/I(\lambda) > S_{U}/I_1(\lambda)$ in FIG. 3D.

As described above, according to the first embodiment, the combined illumination light having a ratio of the spectral intensity of the entire ultraviolet spectrum to the spectral intensity at wavelength $\lambda$ of the visible region adjusted to a desired value can be produced by using the first and second illumination units 3, 4 and the weight coefficient $A(\lambda)$.

Figure 5:
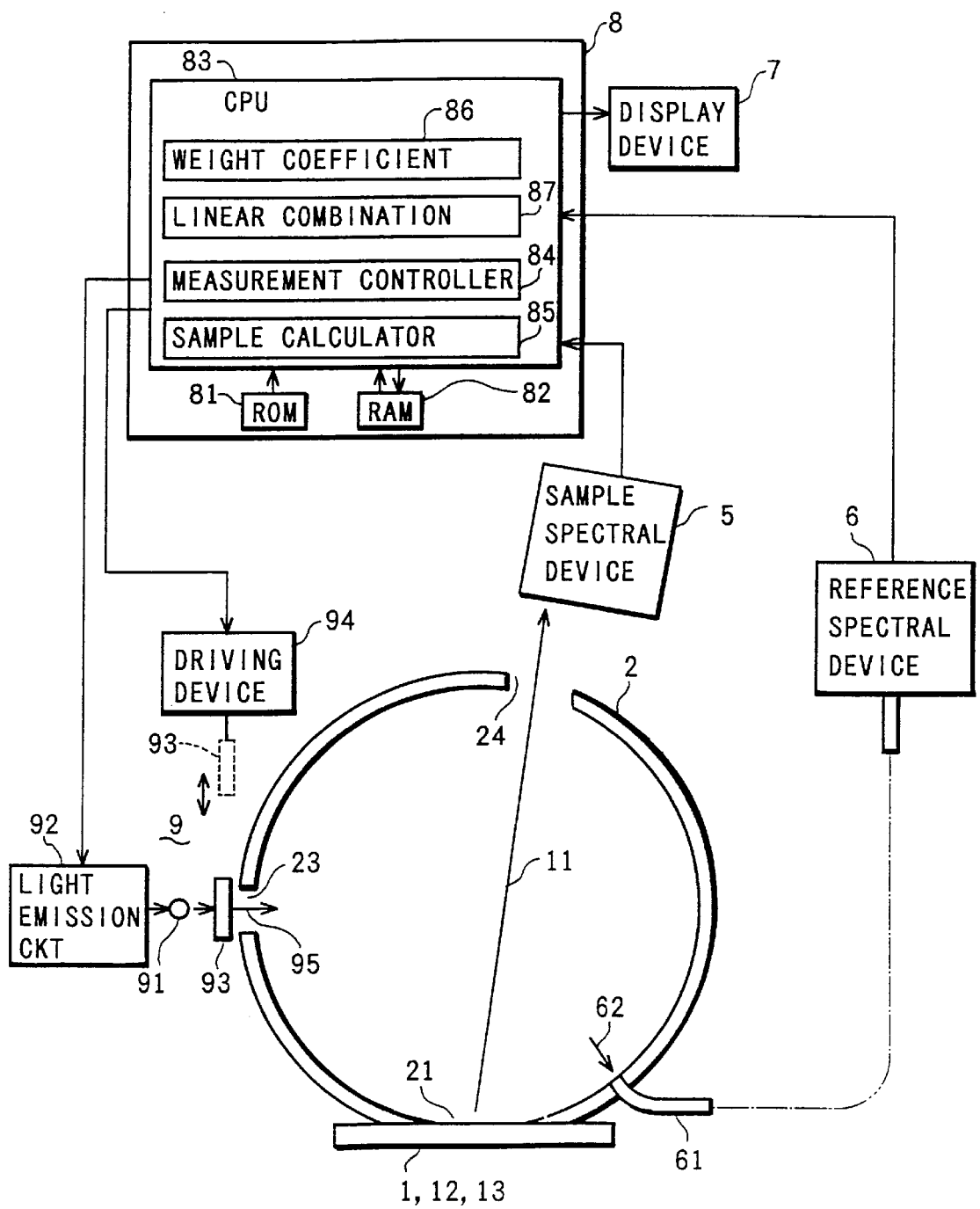
FIG. 5 is a diagram showing a construction of an apparatus for measuring spectral characteristics of a fluorescent sample, according to a second embodiment of the invention.

FIG. 5 is a diagram showing a construction of an apparatus for measuring spectral characteristics of a fluorescent sample, according to a second embodiment of the invention.

The second embodiment is provided with a single illumination unit 9 instead of the first and second illumination units 3, 4 of the first embodiment. The illumination unit 9 is comprised of a light source 91, a light emission circuit 92, a cutoff filter 93 and a driving device 94.

The light source 91 is a xenon lamp or the like for emitting a beam having a sufficient ultraviolet intensity, and is arranged at a light source aperture 23 of the integrating sphere 2. The light emission circuit 92 drives the light source 91 to turn it on and off to emit a pulse of light. A pulsed beam 95 is introduced into the integrating sphere 2 through the light source aperture 23.

The cutoff filter 93 transmits only light components in a wavelength range longer than a first cutoff wavelength $\lambda_{C1}$ (e.g., 400 nm in this embodiment) and is movable between an insertion position where it is located on an optical path of the beam 95 and a retracted position where it is retracted from this optical path. The driving device 94 is adapted to move the cutoff filter 93 between the insertion position and the retracted position and is connected with the CPU 83.

The illumination unit 9 has the same function as the first illumination unit 3 of the first embodiment when the cutoff filter 93 is in its retracted position since the beam 95 including light components in the ultraviolet spectrum is introduced into the integrating sphere 2. On the other hand, the illumination unit 9 has the same function as the second illumination unit 4 of the second embodiment when the cutoff filter 93 is in its insertion position since the beam 95 having light components in the ultraviolet spectrum, i.e., light components at and below wavelength 400 nm removed is introduced into the integrating sphere 2.

The measurement controller 84 controls the driving device 94 to move the cutoff filter 93 to the retracted position and the insertion position; controls the light emission circuit 92 in the respective positions to turn the light source 91 to emit the pulsed beam; and stores the spectral intensity data from the same spectral device 5 and the reference spectral device 6 in the RAM 82.

The total spectral radiance factor of the fluorescent sample is calculated in a manner similar to that of the first embodiment by measuring the spectral radiance factors by the illumination light containing the light components in the ultraviolet spectrum and the illumination light not containing such.

The second embodiment has a construction similar to that of the prior art described with reference to FIG. 7 in which the degree of insertion of the ultraviolet cutoff filter is adjusted. Accordingly, the total spectral radiance factor and the like can easily be calculated with accuracy only by replacing the measuring and calculating techniques by those described in the first embodiment in an apparatus having a prior art construction.

Further, the second embodiment is so constructed as to perform the same function as the first embodiment by the illumination device 9 having a single light source 91 instead of the first and second illumination units 3, 4. Accordingly, the number of the light source apertures formed in the integrating sphere 2 can be reduced as compared with the first embodiment, with the result that a more satisfactory diffused light can be produced inside the integrating sphere 2. This leads to an improvement in measurement accuracy. Further, as compared with the first embodiment, a spectral characteristic measuring apparatus having a simpler construction can be realized by reducing the number of parts around the integrating sphere 2.

The present invention is not limited to the foregoing embodiments, but may be embodied in the following manners (1) to (7).

(1) Although the relative intensity in the ultraviolet spectrum is adjusted using the single standard fluorescent sample in the first embodiment, a plurality of standard fluorescent samples may be used. For example, three standard fluorescent samples a, b, c for assessing an ultraviolet region of a light source which are recommended by CIE NO. 51 (Method for Assessing the Quality of Daylight Simulators for Colorimetry) may be used.

In this embodiment, known total spectral radiance factors $Bt_{Da}(\lambda)$, $Bt_{Db}(\lambda)$, $Bt_{Dc}(\lambda)$ of the standard fluorescent samples a, b, c when being illuminated by light for colorimetry (e.g., standard light D65) are stored in the ROM 81 of FIG. 1.

The measurement controller 84 causes the standard fluorescent samples a, b, c to be individually illuminated by the first and second illumination units 3, 4 and the measured spectral intensity data obtained from the sample spectral device 5 and the reference spectral device 6 to be stored in the RAM 82.

The sample calculator 85 calculates the first and second total spectral radiance factors from the respective measured spectral intensity data stored in the RAM 82.

The weight coefficient calculator 86 calculates an optimized weight coefficient $A(\lambda)$ for each wavelength by the least squares method so as to minimize a sum T of squares given by Equation (10) if $d_a(\lambda)$, $d_b(\lambda)$, $d_c(\lambda)$ denote differences between combined spectral radiance factors $Bt_a(\lambda)$, $Bt_b(\lambda)$, $Bt_c(\lambda)$ given by Equation (8) and known total spectral radiance factors $Bt_{Da}(\lambda)$, $Bt_{Db}(\lambda)$, $Bt_{Dc}(\lambda)$ as defined by Equation (9).

$$Bt_a(\lambda)=A(\lambda)\cdot Bt_{a1}(\lambda)+\{1-A(\lambda)\}\cdot Bt_{a2}(\lambda)$$

$$Bt_b(\lambda)=A(\lambda)\cdot Bt_{b1}(\lambda)+\{1-A(\lambda)\}\cdot Bt_{b2}(\lambda)$$

$$Bt_c(\lambda)=A(\lambda)\cdot Bt_{c1}(\lambda)+\{1-A(\lambda)\}\cdot Bt_{c2}(\lambda) \quad (8)$$

wherein $Bt_{a1}(\lambda)$, $Bt_{a2}(\lambda)$ denote first and second spectral radiance factors of the standard sample a, respectively; $Bt_{b1}(\lambda)$, $Bt_{b2}(\lambda)$ denote first and second total spectral radiance factors of the standard sample b, respectively; and $Bt_{c1}(\lambda)$, $Bt_{c2}(\lambda)$ denote first and second total spectral radiance factors of the standard sample c, respectively.

$$d_a(\lambda)=Bt_a(\lambda)-Bt_{Da}(\lambda)$$

$$d_b(\lambda)=Bt_b(\lambda)-Bt_{Db}(\lambda)$$

$$d_c(\lambda)=Bt_c(\lambda)-Bt_{Dc}(\lambda) \quad (9)$$

$$T=\{d_a(\lambda)\}^2+\{d_b(\lambda)\}^2+\{d_c(\lambda)\}^2 \quad (10)$$

The combined spectral radiance factor weighted by the weight coefficients $A(\lambda)$ obtained in this modification can be used as a total spectral radiance factor for a generally used typical fluorescent brightener without giving rise to a large error. Further, the color values can accurately be calculated from this total spectral radiance factor.

Figure 6:
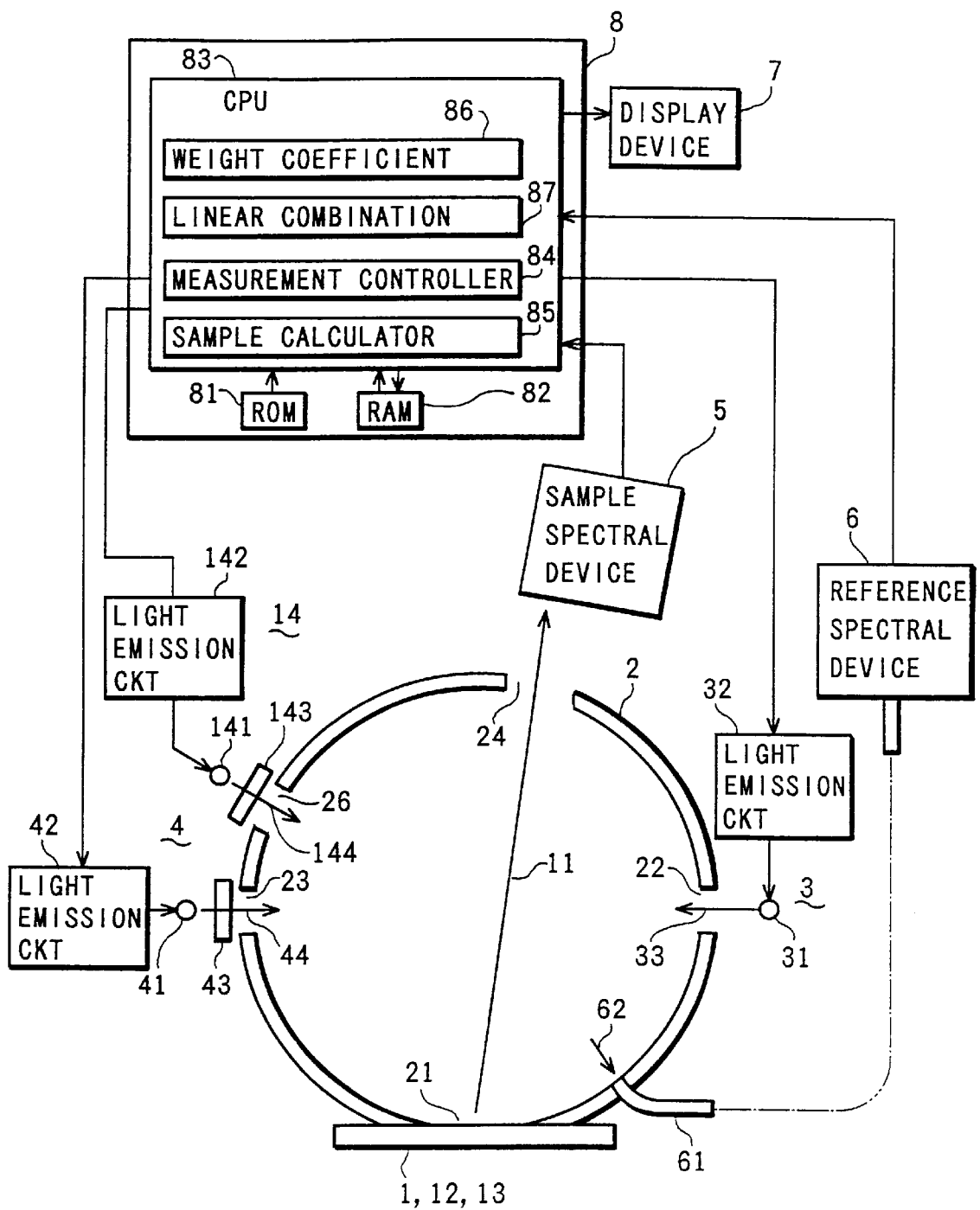
FIG. 6 is a diagram showing a construction of a modified measuring apparatus according to the invention.

(2) In the modification (1), a third illumination unit 14 may be provided in addition to the first and second illumination units 3, 4 as shown in FIG. 6.

The third illumination unit 14 includes a light source 141, a light emission circuit 142 and a cutoff filter 143. The light source 141 is a xenon flash lamp or the like and is arranged at a light source aperture 26 formed in the integrating sphere 2. The cutoff filter 143 is arranged between the light source 141 and the light source aperture 26 and transmits only light components in a wavelength range longer than a second cutoff frequency $\lambda_{C2}(\lambda_{C1}<\lambda_{C2}$, e.g., $\lambda_{C2}$=420 nm). The cutoff filter 143 removes light components in the wavelength range at or below 420 nm from an incident light from the light source 141.

The light emission circuit 142 drives the light source 141 to emit a pulse of light. A pulsed beam 144 having short wavelength components removed by the cutoff filter 143 is introduced into the integrating sphere 2 through the light source aperture 26.

Similar to the modification (1), the measurement controller 84 causes the standard fluorescent samples a, b, c having known total spectral radiance factors $Bt_{Da}(\lambda)$, $Bt_{Db}(\lambda)$, $Bt_{Dc}(\lambda)$ when being illuminated by light for colorimetry (e.g., standard light D65) to be individually illuminated by the first, second and third illumination units 3, 4, 14, thereby obtaining measurement data of the spectral intensities.

Then, the sample calculator 85 calculates the first, second and third total spectral radiance factors of the standard fluorescent samples a, b, c from the respective measurement data.

The weight coefficient calculator 86 calculates optimized first and second weight coefficients $A_1(\lambda)$, $A_2(\lambda)$ for each wavelength by the least squares method so as to minimize a sum U of squares given by Equation (13) if $e_a(\lambda)$, $e_b(\lambda)$, $e_c(\lambda)$ denote differences between combined spectral radiance factors $Bt_a(\lambda)$, $Bt_b(\lambda)$, $Bt_c(\lambda)$ given by Equation (11) and the known total spectral radiance factors $Bt_{Da}(\lambda)$, $Bt_{Db}(\lambda)$, $Bt_{Dc}(\lambda)$ as defined by Equation (12).

$$Bt_a(\lambda)=A_1(\lambda)\cdot Bt_{a1}(\lambda)+A_2(\lambda)\cdot Bt_{a2}(\lambda)+\{1-A_1(\lambda)-A_2(\lambda)\}\cdot Bt_{a3}(\lambda)$$

$$Bt_b(\lambda)=A_1(\lambda)\cdot Bt_{b1}(\lambda)+A_2(\lambda)\cdot Bt_{b2}(\lambda)+\{1-A_1(\lambda)-A_2(\lambda)\}\cdot Bt_{b3}(\lambda)$$

$$Bt_c(\lambda)=A_1(\lambda)\cdot Bt_{c1}(\lambda)+A_2(\lambda)\cdot Bt_{c2}(\lambda)+\{1-A_1(\lambda)-A_2(\lambda)\}\cdot Bt_{c3}(\lambda) \quad (11)$$

wherein $Bt_{a1}(\lambda)$, $Bt_{a2}(\lambda)$, $Bt_{a3}(\lambda)$ denote first, second, third total spectral radiance factors of the standard sample a, respectively; $Bt_{b1}(\lambda)$, $Bt_{b2}(\lambda)$, $Bt_{b3}(\lambda)$ denote first, second, third total spectral radiance factors of the standard sample b, respectively; and $Bt_{c1}(\lambda)$, $Bt_{c2}(\lambda)$, $Bt_{c3}(\lambda)$ denote first, second, third total spectral radiance factors of the standard sample c, respectively.

$$e_a(\lambda)=Bt_a(\lambda)-Bt_{Da}(\lambda)$$

$$e_b(\lambda)=Bt_b(\lambda)-Bt_{Db}(\lambda)$$

$$e_c(\lambda)=Bt_c(\lambda)-Bt_{Dc}(\lambda) \quad (12)$$

$$U=\{e_a(\lambda)\}^2+\{e_b(\lambda)\}^2+\{e_c(\lambda)\}^2 \quad (13)$$

According to this modification, an error in the measurement result can further be reduced by providing the third illumination unit 14, enabling a high accuracy measurement.

(3) Visual characteristics of white fluorescent samples such as fiber and paper containing a fluorescent brightener are often simply expressed by CIE whiteness and tints. Many of the standard fluorescent samples are also expressed by the CIE whiteness and tints.

Accordingly, in this modification, only the known CIE whiteness and tints of the standard fluorescent sample 13 when being illuminated by light for colorimetry (e.g., standard light D65) are stored in the ROM 81 of FIG. 1.

The CIE whiteness and tints are given by Equation (16) using tristimulus values given by equations (14), (15).

$$X=\int x(\lambda)\cdot B_t(\lambda)d\lambda$$

$$Y=\int y(\lambda)\cdot B_t(\lambda)d\lambda$$

$$Z=\int z(\lambda)\cdot B_t(\lambda)d\lambda \quad (14)$$

wherein $x(\lambda)$, $y(\lambda)$, $z(\lambda)$ denote standard observer's isochromatic functions defined by the CIE, $Bt(\lambda)$ denotes the total spectral radiance factor of the sample, and X, Y, Z denote tristimulus values of the sample.

$$x=X/(X+Y+Z)$$

$$y=Y/(X+Y+Z)$$

$$xn=Xn/(Xn+Yn+Zn)$$

$$yn=Yn/(Xn+Yn+Zn) \quad (15)$$

wherein Xn, Yn, Zn denote tristimulus values of the illumination light, x, y denote color values (chromaticity coordinates) of the sample, and xn, yn denote color values (chromaticity coordinates) of the illumination light.

$$WI=Y+800(xn-x)+1700(yn-y)$$

$$\text{Tint}=900(xn-x)-650(yn-y) \quad (16)$$

wherein WI denote CIE whiteness and Tint denote a tint.

In this case, the weight coefficient $A(\lambda)$ can be calculated by defining the weight coefficient $A(\lambda)$ as in Equation (17) and determining constants a, b such that only the CIE whiteness and tints calculated from the total spectral radiance factor $Bt(\lambda)$ in accordance with Equation (6) agree with or approximate to the respective known values of the standard fluorescent sample.

$$A(\lambda)=F(\lambda, a, b) \quad \ldots(17)$$

wherein $F(\lambda, a, b)$ is a function of a wavelength $\lambda$ determined by two constants a, b.

As a function $F(\lambda, a, b)$ can be used, for example, a simple linear function as defined by Equation (18).

$$F(\lambda, a, b)=a\cdot\lambda+b \quad (18)$$

By using such a simple linear function as above, the weight coefficient $A(\lambda)$ can easily be calculated by a simple operation.

In this modification, the weight coefficient $A(\lambda)$ is not calculated such that the total spectral radiance factor $Bt(\lambda)$ of the standard fluorescent sample agrees with the known total spectral radiance factor $Bt_D(\lambda)$ when the sample is illuminated by the light for colorimetry. Accordingly, other color values such as CIE color values and L*a*b* color values can not necessarily be calculated with high accuracy.

However, the total spectral radiance factor $Bt(\lambda)$ can be approximated to the known total spectral radiance factor $Bt_D(\lambda)$ when the sample is illumination by the light for colorimetry by using a function suitable for a difference in spectral intensity between the illumination lights obtained by the first and second illumination units 3, 4 and the light for supposed colorimetry (e.g., standard light D65) as function $F(\lambda, a, b)$. Thus, in this case, other color values can also accurately be calculated.

(4) Although the weight coefficient $A(\lambda)$ dependent on wavelength is used in the foregoing embodiment, a weight coefficient A independent of wavelength may be used.

In this case, a standard fluorescent sample having one or a plurality of known indices (e.g., CIE whiteness) when being illuminated by light for colorimetry (e.g., standard light D65), and the weight coefficient A may be calculated so that the above index or indices calculated from the total spectral radiance factor $Bt(\lambda)$ given by replacing $A(\lambda)$ of Equation (6) by A approach(es) the known value(s).

According to this modification, the method for calculating the weight coefficient is substantially similar to the conventional adjustment by the degree of insertion of the filter described with reference to FIG. 7. However, this modification is better than the prior art apparatus in that it has a simpler construction without having a movable portion and it hardly requires a time for the adjustment. Thus, measurement operability can be imp roved.

(5) The adjustment of the relative ultraviolet intensity is numerically conducted by the weight coefficient. By calculating weight coefficients $A_D(\lambda)$, $A_A(\lambda)$, $A_F(\lambda)$ corresponding to a plurality of lights for colorimetry, e.g., standard lights D65, A and light F of a fluorescent lamp and storing them in advance, the total spectral radiance factors and color values when illumination is made by all the above lights for colorimetry can be calculated by one measurement. One fluorescent sample can be assessed by a plurality of lights for colorimetry.

(6) Although the weight coefficient is calculated such that the combined total spectral radiance factor approaches the known total spectral radiance factor when illumination is made by light for colorimetry in the modifications (1), (2), it may be calculated such that the color value obtained from the combined total spectral radiance factor approaches such a color value obtained from a known total spectral radiance factor.

For example, the weight coefficient is expressed by a function of wavelength and a suitable constant, and known color values, e.g., tristimulus values $X_{Da}$, $Y_{Da}$, $Z_{Da}$ (standard fluorescent sample a), $X_{Db}$, $Y_{Db}$, $Z_{Db}$ (standard fluorescent sample b), $X_{Dc}$, $Y_{Dc}$, $Z_{Dc}$ (standard fluorescent sample c) of the standard fluorescent samples a, b, c when illumination is made by light for colorimetry are stored. The weight coefficient $A(\lambda)$ may be calculated for each wavelength by calculating the constant of the function so as to minimize a sum T (shown in Equation (19)) of squares of differences between the tristimulus values $X_a$, $Y_a$, $Z_a$, $X_b$, $Y_b$, $Z_b$, $X_c$, $Y_c$, $Z_c$ obtained from the combined total spectral radiance factors $Bt_a(\lambda)$, $Bt_b(\lambda)$, $Bt_c(\lambda)$ calculated from the measured first and second total spectral radiance factors and the weight coefficient in the modification or from the measured first, second and third spectral radiance factors and the first and second weight coefficient in the modification (2).

$$t = (X_a - X_{Da})^2 + (Y_a - Y_{Da})^2 + \\ (Z_a - Z_{Da})^2 + (X_b - X_{Db})^2 + (Y_b - Y_{Db})^2 + \\ (Z_b - Z_{Db})^2 + (X_c - X_{Dc})^2 + (Y_c - Y_{Dc})^2 + (Z_c - Z_{Dc})^2 \quad (19)$$

The combined total spectral radiance factor weighted by the weight coefficient $A(\lambda)$ obtained in this modification can reduce the degree of an error in the color values obtained from the tristimulus values X, Y, Z smaller than in the modifications (1), (2) for generally used typical fluorescent brighteners.

(7) Although the illumination unit for emitting light having no light components in the ultraviolet spectrum is constructed by setting the first cutoff frequency $\lambda_{C1}$ of the cutoff filters 43, 93 at 400 nm in the foregoing embodiments, similar effects can be obtained even if two illumination units having different ultraviolet intensities are used by setting $\lambda_{C1}$ at, e.g., 370 nm to transmit light components in the ultraviolet spectrum to a certain degree.

As described above, the first total spectral radiance factor of the fluorescent sample placed in the measurement position is measured by illuminating it by the first illumination device for emitting a beam in a wavelength range including the ultraviolet spectrum, and the second total spectral radiance factor of the fluorescent sample is measured by illuminating it by the second illumination device for emitting a beam in a wavelength range longer than the first cutoff wavelength. The total spectral radiance factor of the fluorescent sample is calculated in accordance with the following equation using the measured first and second total spectral radiance factors and the weight coefficient for weighting the first and second total spectral radiance factor which is calculated for each wavelength. Accordingly, the total spectral radiance factor of the fluorescent sample can accurately be calculated by a simple construction having no movable portion within a short time.

$$B_t(\lambda) = A(\lambda) \cdot Bt_1(\lambda) + \{1 - A(\lambda)\} \cdot Bt_2(\lambda)$$

wherein:
Bt($\lambda$): Total spectral radiance factor of the fluorescent sample
A($\lambda$): Weight coefficient
$Bt_1(\lambda)$: First total spectral radiance factor
$Bt_2(\lambda)$: Second total spectral radiance factor Further, the known total spectral radiance factor of the standard fluorescent sample when being illuminated by light for colorimetry having a specified spectral intensity is stored. The first total spectral radiance factor of the standard fluorescent sample placed in the measurement position is measured by illuminating it by the first illumination device, and the second total spectral radiance factor of the standard fluorescent sample is measured by illuminating it by the second illumination device. The weight coefficient is calculated for each wavelength so as to satisfy the following equation using the measured first and second total spectral radiance factors of the standard fluorescent sample and the stored known total spectral radiance factor thereof and is stored. Accordingly, the total spectral radiance factor calculated using this weight coefficient can be caused to substantially agree with the total spectral radiance factor of the fluorescent sample when illumination is made by light for colorimetry for the fluorescent sample including a fluorescent dye or fluorescent pigment analogous to the standard fluorescent sample.

$$Bt_D(\lambda) \approx A(\lambda) \cdot Bt_1(\lambda) + \{1 - A(\lambda)\} \cdot Bt_2(\lambda)$$

wherein:
$Bt_D(\lambda)$: Known total spectral radiance factor of the standard fluorescent sample
A($\lambda$): Weight coefficient
$Bt_1(\lambda)$: First total spectral radiance factor of the standard fluorescent sample
$Bt_2(\lambda)$: Second total spectral radiance factor of the standard fluorescent sample Further, known total spectral radiance factors of n standard fluorescent samples when illumination is made by light for colorimetry having a specified spectral intensity are stored. The first total spectral radiance factors of the n standard fluorescent samples are measured by illuminating the n fluorescent samples placed one after another in the measurement position by the first illumination device, and the second total spectral radiance factors thereof are measured by illuminating the n standard fluorescent samples by the first illumination device. By calculating the weight coefficient for each wavelength such that a sum of respective squares of differences between the combined total spectral radiance factors of the standard fluorescent samples given by the following equation using the measured first and second total spectral radiance factors thereof and the weight coefficient and the known total spectral radiance factors thereof, the total spectral radiance factor calculated using the weight coefficient can accurately be approximated to the total spectral radiance factor when illumination is made by the light for colorimetry.

$$Bt_i(\lambda) = A(\lambda) \cdot Bt_{i1}(\lambda) + \{1 - A(\lambda)\} \cdot Bt_{i2}(\lambda)$$

wherein:
i: 1 to n
$Bt_i(\lambda)$: Combined total spectral radiance factor of the i-th standard fluorescent sample
A($\lambda$): Weight coefficient
$Bt_{i1}(\lambda)$: First spectral radiance factor of the i-th standard fluorescent sample
$Bt_{i2}(\lambda)$: Second spectral radiance factor of the i-th standard fluorescent sample The weight coefficient is expressed by a function of a wavelength and two constants. Known CIE whiteness and tints of the standard fluorescent sample when being illuminated by light for colorimetry having a specified spectral intensity are stored. The first total spectral radiance factor of the standard fluorescent sample placed in the measurement position is measured by illuminating it by the first illumination device, and the second total spectral radiance factor thereof is measured by illuminating it by the second illumination device. The weight coefficient is calculated for each wavelength by calculating two constants such that the CIE whiteness and tints calculated from the combined total spectral radiance factor given by the following equation using the measured first and second total spectral radiance factors approach the stored known CIE whiteness and tints. Accordingly, the CIE whiteness and tints calculated from the total spectral radiance factor obtained using this weight coefficient can be caused to substantially agree with the CIE whiteness and tints of the fluorescent sample when being illuminated by the light for colorimetry for the fluorescent sample containing a fluorescent dye or fluorescent pigment analogous to the standard fluorescent sample.

$$Bt(\lambda) = A(\lambda) \cdot Bt_1(\lambda) + \{1 - A(\lambda)\} \cdot Bt_2(\lambda)$$

wherein:

Bt($\lambda$): Combined spectral radiance factor

A($\lambda$): Weight coefficient $Bt_1(\lambda)$: First total spectral radiance factor of the standard fluorescent sample $Bt_2(\lambda)$: Second total spectral radiance factor of the standard fluorescent sample The first and second illumination device may be constructed by a single light source for emitting a beam in a wavelength range including the ultraviolet spectrum, a cutoff filter movably arranged between the insertion position on the optical path of the illumination light from the light source and the retracted position retracted from the optical path for blocking light components in a wavelength range at or below the first cutoff wavelength, and the driving device for moving the cutoff filter between the insertion position and the retracted position. The first total spectral radiance factor of the fluorescent sample is measured by turning the light source on with the cutoff filter in its retracted position, whereas the second total spectral radiance factor thereof is measured by turning the light source on with the cutoff filter in its insertion position. Accordingly, the total spectral radiance factor of the fluorescent sample can accurately be calculated within a short time in an apparatus having a prior art construction in which the degree of insertion of the cutoff filter is variable.

Further, the first, second and third total spectral radiance factors of the fluorescent sample placed in the measurement position may be measured by the first illumination device for emitting a beam in a wavelength range including the ultraviolet spectrum, the second illumination device for emitting a beam in a wavelength range longer than the first cutoff wavelength, and the third illumination device for emitting a beam in a wavelength range longer than the second cutoff wavelength different from the first cutoff wavelength. In this case, the total spectral radiance factor of the fluorescent sample is calculated in accordance with the following equation using the measured first, second and third total spectral radiance factors and the first and second weight coefficients obtained for each wavelength to weight the first, second and third total spectral radiance factors. Therefore, the total spectral radiance factor of the fluorescent sample can accurately be calculated within a short time by a simple construction having no movable portion.

$$Bt(\lambda)=A_1(\lambda)\cdot Bt_1(\lambda)+A_2(\lambda)\cdot Bt_2(\lambda)+\{1-A_1(\lambda)-A_2(\lambda)\}\cdot Bt_3(\lambda)$$

wherein:

Bt($\lambda$): Total spectral radiance factor of fluorescent sample $A_1(\lambda)$: First weight coefficient $A_2(\lambda)$: Second weight coefficient $Bt_1(\lambda)$: First total spectral radiance factor $Bt_2(\lambda)$: Second total spectral radiance factor $Bt_1(\lambda)$: Third total spectral radiance factor.

The known total spectral radiance factors of n standard fluorescent samples when being illustrated by light for colorimetry having a specified spectral intensity are stored. The first, second and third total spectral radiance factors of the n standard fluorescent samples are measured by illuminating them placed in the measurement position one after another by the first, second and third illumination device, respectively. By calculating the weight coefficients for each wavelength so as to minimize a sum of respective squares of differences between the combined total spectral radiance factor given by the following equation made up of the first, second and third total spectral radiance factors and the weight coefficients and the known total spectral radiance factors of the standard fluorescent samples, the total spectral radiance factor calculated using the weight coefficients can accurately be approximated to the total spectral radiance factor when illumination is made by the light for colorimetry.

$$Bt_i(\lambda)=A_1(\lambda)\cdot Bt_{i1}(\lambda)+A_2(\lambda)\cdot Bt_{i2}(\lambda)+\{1-A_1(\lambda)-A_2(\lambda)\}\cdot Bt_{i3}(\lambda)$$

wherein:

i: 1 to n $Bt_i(\lambda)$: Total spectral radiance factor of the i-th fluorescent sample $A_1(\lambda)$: First weight coefficient $A_2(\lambda)$: Second weight coefficient $Bt_{i1}(\lambda)$: First total spectral radiance factor of the i-th standard fluorescent sample $Bt_{i2}(\lambda)$: Second total spectral radiance factor of the i-th standard fluorescent sample $Bt_{i3}(\lambda)$: Third total spectral radiance factor of the i-th standard fluorescent sample The known total spectral radiance factors of n standard fluorescent samples when being illuminated by light for colorimetry having a specified spectral intensity are stored. The weight coefficients are calculated for each wavelength by calculating the constant of the function so as to minimize a sum of respective squares of differences between the color values calculated from the measured first and second total spectral radiance factors of the standard fluorescent samples and the weight coefficient or from the measured first, second and third total spectral radiance factors of the standard fluorescent samples and the first and second weight coefficients and the known color values of the standard fluorescent samples and stored in the storage device. Therefore, the color values obtained from the combined total spectral radiance factor calculated using the weight coefficients can accurately be approximated to the color values obtained when illumination is made by the light for colorimetry.

By setting the first cutoff wavelength at the shortest wavelength of the visible spectrum, a beam having no light components in the ultraviolet spectrum is emitted. Accordingly, the relative intensity in the ultraviolet spectrum can equivalently be adjusted by the first and second illumination device and the weight coefficients. A first spectral characteristic value of a fluorescent sample placed in a measurement position is measured by illuminating the fluorescent sample by a first illumination device which emits a beam in a wavelength range including the ultraviolet spectrum, and a second spectral characteristic value of the fluorescent sample is measured by illuminating the fluorescent sample by a second illumination device which emits a beam in a wavelength excluding the ultraviolet spectrum. A total spectral characteristic value of the fluorescent sample is calculated based on measured first and second spectral characteristic values and a weight coefficient. The weight coefficient is calculated so as to minimize a sum of respective squares of differences between total spectral characteristic values of a plurality of standard fluorescent samples and known total spectral characteristic values of the plurality of standard fluorescent samples. Accordingly, a total spectral characteristic values of a fluorescent sample can be accurately calculated by a simple construction having no movable portion within a short time.

The first and second total spectral radiance factors of the fluorescent sample placed in the measurement position are measured by the first illumination device for emitting a beam in a wavelength range including the ultraviolet spectrum and the second illumination device for emitting a beam in a wavelength range longer than the first cutoff wavelength. The total spectral radiance factor of the fluorescent sample is calculated in accordance with the following equation using the weight coefficient obtained for each wavelength to weight the first and second total spectral radiance factors and the measured first and second total spectral radiance factors. Therefore, the total spectral radiance factor of the fluorescent sample can accurately be calculated within a short time.

$$Bt(\lambda)=A(\lambda)\cdot Bt_1(\lambda)+\{1-A(\lambda)\}\cdot Bt_2(\lambda)$$

wherein:
- $Bt(\lambda)$: Total spectral radiance factor of fluorescent sample
- $A(\lambda)$: Weight coefficient
- $Bt1(\lambda)$: First total spectral radiance factor
- $Bt2(\lambda)$: Second total spectral radiance factor Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

What is claimed is:

1. An apparatus for measuring a spectral characteristic of a fluorescent sample, comprising:
    a first illumination device which emits a beam in a wavelength range including the ultraviolet spectrum;
    a second illumination device which emits a beam in a wavelength range longer than a first cutoff wavelength;
    a spectral radiance factor measuring device which measures a first total spectral radiance factor of a fluorescent sample placed in a measurement position by illuminating the fluorescent sample by the first illumination device, and a second total spectral radiance factor of the fluorescent sample by illuminating the fluorescent sample by the second illumination device;
    a storage device which stores weight coefficients for weighting first and second total spectral radiance factors, each weight coefficient being calculated for each wavelength; and
    a calculator which calculates a total spectral radiance factor of the fluorescent sample in accordance with the following equation using measured first and second total spectral radiance factors and a weight coefficient:

$$B_t(\lambda)=A(\lambda)\cdot Bt_1(\lambda)+\{1-A(\lambda)\}\cdot Bt_2(\lambda)$$

wherein:
- $Bt(\lambda)$: Total spectral radiance factor of the fluorescent sample
- $A(\lambda)$: Weight coefficient
- $Bt_1(\lambda)$: First total spectral radiance factor
- $Bt_2(\lambda)$: Second total spectral radiance factor.

2. An apparatus according to claim 1, further comprising a weight coefficient calculator which calculates a weight coefficient to be stored in the storage device, wherein;
    the storage device further stores a known total spectral radiance factor of a standard fluorescent sample when being illuminated by light having a predetermined spectral intensity;
    the spectral radiance factor measuring device further measures a first total spectral radiance factor of the standard fluorescent sample placed in the measurement position by illuminating the standard fluorescent sample by the first illumination device, and measures a second total spectral radiance factor of the standard fluorescent sample by illuminating the standard fluorescent sample by the second illumination device;
    the weight coefficient calculator calculates a weight coefficient for each wavelength so as to satisfy the following equation using measured first and second total spectral radiance factors and the stored known total spectral radiance factor of the standard fluorescent sample:

$$Bt_D(\lambda)\approx A(\lambda)\cdot Bt_1(\lambda)+\{1-A(\lambda)\}\cdot Bt_2(\lambda)$$

wherein:
- $Bt_D(\lambda)$: Known total spectral radiance factor of the standard fluorescent sample
- $A(\lambda)$: Weight coefficient
- $Bt_1(\lambda)$: First total spectral radiance factor of the standard fluorescent sample
- $Bt_2(\lambda)$: Second total spectral radiance factor of the standard fluorescent sample.

3. An apparatus according to claim 1, further comprising a weight coefficient calculator which calculates a weight coefficient to be stored in the storage device, wherein;
    the storage device further stores known total spectral radiance factors of n standard fluorescent samples when being illuminated by light having a predetermined spectral intensity;
    the spectral radiance factor measuring device further measures first and second total spectral radiance factors of the n standard fluorescent samples placed one after another in the measurement position by illuminating the standard fluorescent sample by the first and second illumination device, respectively;
    the weight coefficient calculator calculates a weight coefficient for each wavelength so as to minimize a sum of respective squares of differences between combined total spectral radiance factors of the standard fluorescent samples given by the following equation including measured first and second total spectral radiance factors of each standard fluorescent sample and the weight coefficient, and the known total spectral radiance factor of each standard fluorescent sample:

$$Bt_i(\lambda)=A(\lambda)\cdot Bt_{i1}(\lambda)+\{1-A(\lambda)\}\cdot Bt_{i2}(\lambda) \text{ wherein:}$$

i: 1 to n
- $Bt_i(\lambda)$: Combined total spectral radiance factor of the i-th standard fluorescent sample
- $A(\lambda)$: Weight coefficient
- $Bt_{i1}(\lambda)$: First spectral radiance factor of the i-th standard fluorescent sample
- $Bt_{i2}(\lambda)$: Second spectral radiance factor of the i-th standard fluorescent sample.

4. An apparatus according to claim 3, wherein: the storage device further stores known color values of the n standard fluorescent samples when being illuminated by light having a specified spectral intensity;
    the weight coefficient being expressed by a function of a wavelength and constants;
    the weight coefficient calculator calculates weight coefficients for each wavelength by calculating constants of the function so as to minimize a sum of respective squares of differences between color values calculated from a combined total spectral radiance factor using the measured first and second total spectral radiance factors and the weight coefficient of the standard fluorescent samples and the known color values of the standard fluorescent samples.

5. An apparatus according to claim 1, further comprising a weight coefficient calculator which calculates a weight coefficient to be stored in the storage device, the weight coefficient being expressed by a function of a wavelength and two constants, wherein;

the storage device further stores known CIE whiteness and tints of a standard fluorescent sample when being illuminated by light having a specified spectral intensity;

the spectral radiance factor measuring device further measures a first total spectral radiance factor of the standard fluorescent sample placed in the measurement position by illuminating the standard fluorescent sample by the first illumination device, and a second total spectral radiance factor of the standard fluorescent sample by illuminating the standard fluorescent sample by the second illumination device;

the weight coefficient calculator calculates a weight coefficient for each wavelength by calculating two constants such that the CIE whiteness and tints calculated from a combined total spectral radiance factor given by the following equation using measured first and second total spectral radiance factors approach the stored known CIE whiteness and tints:

$$Bt(\lambda)=A(\lambda) \cdot Bt_1(\lambda)+\{1-A(\lambda)\} \cdot Bt_2(\lambda)$$

wherein:
$Bt(\lambda)$: Combined spectral radiance factor
$A(\lambda)$: Weight coefficient
$Bt_1(\lambda)$: First total spectral radiance factor of the standard fluorescent sample
$Bt_2(\lambda)$: Second total spectral radiance factor of the standard fluorescent sample.

6. An apparatus according to claim 5, wherein the weight coefficient $A(\lambda)$ is expressed by the following equation:

$$A(\lambda)=a+b \cdot \lambda$$

wherein a and b denote constants, respectively.

7. An apparatus according to claim 1, wherein:
the first and second illumination device commonly includes:
a single light source for emitting a beam in a wavelength range including the ultraviolet spectrum;
a cutoff filter movably arranged between an insertion position into an optical path of illumination light from the light source and a retracted position from the optical path for blocking light components in a wavelength range at or below the first cutoff wavelength; and
a driver for moving the cutoff filter between the insertion position and the retracted position;
the spectral radiance factor measuring device measures a first total spectral radiance factor of the fluorescent sample by turning the light source on with the cutoff filter in its retracted position, and a second total spectral radiance factor of the fluorescent sample by turning the light source on with the cutoff filter in its insertion position.

8. An apparatus according to claim 1, wherein the first cutoff wavelength is set at a shortest wavelength of the visible spectrum.

9. An apparatus for measuring a spectral characteristic of a fluorescent sample, comprising:

a first illumination device which emits a beam in a wavelength range including the ultraviolet spectrum;
a second illumination device which emits a beam in a wavelength range longer than a first cutoff wavelength;
a third illumination device which emits a beam in a wavelength range longer than a second cutoff wavelength different from the first cutoff wavelength;
a spectral radiance factor measuring device which measures a first total spectral radiance factor of a fluorescent sample placed in a measurement position by illuminating the fluorescent sample by the first illumination device, and a second total spectral radiance factor of the fluorescent sample by illuminating the fluorescent sample by the second illumination device, and a third total spectral radiance factor of the fluorescent sample by illuminating the fluorescent sample by the third illumination device;
a storage device which stores first and second weight coefficients for weighting first, second, and third total spectral radiance factors, the first and second weight coefficients being calculated for each wavelength; and
a calculator which calculates a total spectral radiance factor of the fluorescent sample in accordance with the following equation using measured first, second, and third total spectral radiance factors and the first and second weight coefficients:

$$Bt(\lambda)=A_1(\lambda) \cdot Bt_1(\lambda)+A_2(\lambda) \cdot Bt_2(\lambda)+\{1-A_1(\lambda)-A_2(\lambda)\} \cdot Bt_3(\lambda)$$

wherein:
$Bt(\lambda)$: Total spectral radiance factor of the fluorescent sample
$A_1(\lambda)$: First weight coefficient
$A_2(\lambda)$: Second weight coefficient
$Bt_1(\lambda)$: First total spectral radiance factor
$Bt_2(\lambda)$: Second total spectral radiance factor
$Bt_3(\lambda)$: Third total spectral radiance factor.

10. An apparatus according to claim 9, further comprising a weight coefficient calculator which calculates first and second weight coefficients to be stored in the storage device, wherein;

the storage device further stores known total spectral radiance factors of n standard fluorescent samples when being illuminated by light having a specified spectral intensity;

the spectral radiance factor measuring device measures a first, second and third total spectral radiance factor of the n standard fluorescent samples by illuminating them placed in a measurement position one after another by the first, second and third illumination device, respectively;

the weight coefficient calculator calculates first and second weight coefficients for each wavelength so as to minimize a sum of respective squares of differences between combined total spectral radiance factor given by the following equation made up of the first, second and third total spectral radiance factors and the first and second weight coefficients and the known total spectral radiance factors of the standard fluorescent samples:

$$Bt_i(\lambda)=A_1(\lambda) \cdot Bt_{i1}(\lambda)+A_2(\lambda) \cdot Bt_{i2}(\lambda)+\{1-A_1(\lambda)-A_2(\lambda)\} \cdot Bt_{i3}(\lambda)$$

wherein:
i: 1 to n
$Bt_i(\lambda)$: Total spectral radiance factor of the i-th fluorescent sample
$A_1(\lambda)$: First weight coefficient
$A_2(\lambda)$: Second weight coefficient
$Bt_{i1}(\lambda)$: First total spectral radiance factor of the i-th standard fluorescent sample $Bt_{i2}(\lambda)$: Second total spectral radiance factor of the i-th standard fluorescent sample $Bt_{i3}(\lambda)$: Third total spectral radiance factor of the i-th standard fluorescent sample.

11. An apparatus according to claim 10, wherein:

the storage device further stores known color values of the n standard fluorescent samples when being illuminated by light having a specified spectral intensity;

the weight coefficients being expressed by a function of a wavelength and constants;

the weight coefficient calculator calculates weight coefficients for each wavelength by calculating constants of the function so as to minimize a sum of respective squares of differences between color values calculated from a combined total spectral radiance factor using the measured first, second, and third total spectral radiance factors and the weight coefficient of the standard fluorescent samples and the known color values of the standard fluorescent samples.

12. An apparatus according to claim 9, wherein the first cutoff wavelength is set at a shortest wavelength of the visible spectrum.

13. An apparatus for measuring a spectral characteristic of a fluorescent sample, comprising:

a first illumination device which emits a beam in a wavelength range including the ultraviolet spectrum;

a second illumination device which emits a beam in a wavelength excluding the ultraviolet spectrum;

a measuring device which measures a first spectral characteristic value of a fluorescent sample placed in a measurement position by illuminating the fluorescent sample by the first illumination device and a second spectral characteristic value of the fluorescent sample by illuminating the fluorescent sample by the second illumination device;

a total spectral characteristic value calculator which calculates a total spectral characteristic value of the fluorescent sample using measured first and second spectral characteristic values and a weight coefficient; and a weight coefficient calculator which calculates a weight coefficient for each wavelength to minimize a sum of respective squares of differences between total spectral characteristic values of a plurality of standard fluorescent samples and known total spectral characteristic values of the plurality of standard fluorescent samples.

14. An apparatus according to claim 13, wherein the spectral characteristic value is a spectral radiance factor.

15. A method for measuring a spectral characteristic of a fluorescent sample, comprising the steps of:

measuring a first total spectral radiance factor of a fluorescent sample placed in a measurement position by illuminating the fluorescent sample by a first illumination device emitting a beam in a wavelength range including the ultraviolet spectrum;

measuring a second total spectral radiance factor of the fluorescent sample by illuminating the fluorescent sample by a second illumination device emitting a beam in a wavelength range longer than a first cutoff wavelength;

calculating a total spectral radiance factor of the fluorescent sample in accordance with the following equation using measured first and second total spectral radiance factors and a weight coefficient:

$$B_t(\lambda) = A(\lambda) \cdot Bt_1(\lambda) + \{1 - A(\lambda)\} \cdot Bt_2(\lambda)$$

wherein:

$Bt(\lambda)$: Total spectral radiance factor of the fluorescent sample $A(\lambda)$: Weight coefficient $Bt_1(\lambda)$: First total spectral radiance factor $Bt_2(\lambda)$: Second total spectral radiance factor.

16. A method according to claim 15, further comprising the steps of:

measuring first and second total spectral radiance factors of n standard fluorescent samples placed one after another in the measurement position by illuminating the standard fluorescent sample by the first and second illumination device, respectively;

calculating a weight coefficient for each wavelength so as to minimize a sum of respective squares of differences between combined total spectral radiance factors of the standard fluorescent samples given by the following equation including measured first and second total spectral radiance factors of each standard fluorescent sample and the weight coefficient, and a known total spectral radiance factor of each standard fluorescent sample:

$$Bt_i(\lambda) = A(\lambda) \cdot Bt_{i1}(\lambda) + \{1 - A(\lambda)\} \cdot Bt_{i2}(\lambda)$$

wherein:

i: 1 to n $Bt_i(\lambda)$: Combined total spectral radiance factor of the i-th fluorescent sample $A(\lambda)$: Weight coefficient $Bt_{i1}(\lambda)$: First spectral radiance factor of the i-th standard fluorescent sample $Bt_{i2}(\lambda)$: Second spectral radiance factor of the i-th standard fluorescent sample.

17. A method for measuring a spectral characteristic of a fluorescent sample, comprising the steps of:

measuring a first total spectral radiance factor of a fluorescent sample placed in a measurement position by illuminating the fluorescent sample by a first illumination device emitting a beam in a wavelength range including the ultraviolet spectrum;

measuring a second total spectral radiance factor of the fluorescent sample by illuminating the fluorescent sample by a second illumination device emitting a beam in a wavelength range longer than a first cutoff wavelength;

measuring a third total spectral radiance factor of the fluorescent sample by illuminating the fluorescent sample by a third illumination device emitting a beam in a wavelength range longer than a second cutoff wavelength different from the first cutoff wavelength; and calculating a total spectral radiance factor of the fluorescent sample in accordance with the following equation using measured first, second, and third total spectral radiance factors and first and second weight coefficients:

$$Bt(\lambda) = A_1(\lambda) \cdot Bt_1(\lambda) + A_2(\lambda) \cdot Bt_2(\lambda) + \{1 - A_1(\lambda) - A_2(\lambda)\} \cdot Bt_3(\lambda)$$

wherein:

$Bt(\lambda)$: Total spectral radiance factor of the fluorescent sample $A_1(\lambda)$: First weight coefficient $A_2(\lambda)$: Second weight coefficient $Bt_1(\lambda)$: First total spectral radiance factor $Bt_2(\lambda)$: Second total spectral radiance factor $Bt_3(\lambda)$: Third total spectral radiance factor.

* * * * *